(12) United States Patent
Franzen (10) Patent No.: US 10,166,356 B2
(45) Date of Patent: Jan. 1, 2019

(54) REVERSIBLE FRAME FOR A PATIENT INTERFACE ASSEMBLY

(71) Applicant: KONINKLIJKE PHILIPS N.V., Eindhoven (NL)

(72) Inventor: Erika Franzen, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1045 days.

(21) Appl. No.: 14/408,575

(22) PCT Filed: Jun. 19, 2013

(86) PCT No.: PCT/IB2013/055025
§ 371 (c)(1),
(2) Date: Dec. 17, 2014

(87) PCT Pub. No.: WO2013/190480
PCT Pub. Date: Dec. 27, 2013

(65) Prior Publication Data
US 2015/0182718 A1  Jul. 2, 2015

Related U.S. Application Data

(60) Provisional application No. 61/661,839, filed on Jun. 20, 2012.

(51) Int. Cl.
*A61M 16/06* (2006.01)

(52) U.S. Cl.
CPC .... *A61M 16/0622* (2014.02); *A61M 16/0683* (2013.01); *A61M 16/06* (2013.01); *A61M 2210/0618* (2013.01)

(58) Field of Classification Search
CPC ........... A61M 16/06–16/0627; A61M 16/0683
See application file for complete search history.

(56) References Cited

U.S. PATENT DOCUMENTS 5,093,940 A * 3/1992 Nishiyama ................ A61F 9/02
2/440
8,291,285 B1   10/2012 Henry
(Continued)

FOREIGN PATENT DOCUMENTS

CN    101237902 A    8/2008
CN    101516300 A    8/2009
(Continued)

OTHER PUBLICATIONS

"Hope 2 Sleep—Optilife CPAP Mask Strap & Mini Hose Covers", http://www.hope2sleep.co.uk/products/18 (Nov. 2014).

*Primary Examiner* — LaToya M Louis
(74) *Attorney, Agent, or Firm* — Michael W. Haas (57) ABSTRACT

A reversible frame assembly includes a body, a cushion assembly coupling, and a reversing device. The body has a first side and a second side. The body includes at least a first body member and a second body member. The body is coupled to a cushion assembly at the cushion assembly coupling with the cushion assembly disposed on one of the first or second sides of the body. The body is structured to be disposed in one of two concave configurations, a first concave configuration, wherein the body first side is concave about at least a portion of the cushion assembly, and a second concave configuration, wherein the body second side is concave about at least a portion of the cushion assembly. The reversing device is structured to allow the body to move between the first configuration and second configuration.

3 Claims, 5 Drawing Sheets

(56) References Cited

U.S. PATENT DOCUMENTS

| | | | |
|---|---|---|---|
| 8,550,084 B2 * | 10/2013 | Ng | A61M 16/06 |
| | | | 128/206.28 |
| 8,616,203 B2 | 12/2013 | Jaffe | |
| 9,032,955 B2 | 5/2015 | Lubke | |
| 2006/0174891 A1 | 8/2006 | Ammann | |
| 2008/0047560 A1 | 2/2008 | Veliss | |
| 2008/0060649 A1 | 3/2008 | Veliss | |
| 2009/0145437 A1 | 6/2009 | Halpern | |
| 2009/0183739 A1 | 7/2009 | Wondka | |
| 2010/0018534 A1 | 1/2010 | Veliss | |
| 2011/0088699 A1 | 4/2011 | Skipper | |

FOREIGN PATENT DOCUMENTS

| | | |
|---|---|---|
| EP | 1658873 A1 | 5/2006 |
| JP | 2009544372 A | 12/2009 |
| JP | 2010512193 A | 4/2010 |
| WO | WO0205883 A1 | 1/2002 |
| WO | WO2007048174 A1 | 5/2007 |
| WO | WO2009108995 A1 | 9/2009 |
| WO | WO2009139647 A1 | 11/2009 |
| WO | WO2011121466 A1 | 10/2011 |
| WO | WO2012028995 A1 | 3/2012 |

\* cited by examiner

REVERSIBLE FRAME FOR A PATIENT INTERFACE ASSEMBLY

CROSS-REFERENCE TO RELATED APPLICATIONS

This patent application claims the priority benefit under 35 U.S.C. § 371 of international patent application no. PCT/IB2013/055025, filed Jun. 19, 2013, which claims the priority benefit under 35 U.S.C. § 119(e) of U.S. Provisional Application No. 61/661,839 filed on Jun. 20, 2012, the contents of which are herein incorporated by reference.

BACKGROUND OF THE INVENTION

1. Field of the Invention

The present invention relates to a patient interface assembly for communicating a flow of gas with an airway of a user which includes, but is not limited to, a patient interface device that includes a patient contacting cushion and a reversible support frame that is part of a support assembly.

2. Description of the Related Art

A conventional patient interface device may include a relatively rigid faceplate and a softer patient contacting cushion or cushion assembly. A flexible faceplate may act as or otherwise be part of a patient contacting cushion or patient contacting cushion assembly. Hereinafter, however, this description shall refer to a patient contacting cushion assembly, but it is understood that the patient contacting cushion may be a flexible faceplate as well. The patient contacting cushion is made from a relatively soft material that is structured to substantially adapt to the contour of the user's face. Thus, the patient contacting cushion creates a generally continuous seal about the user's nose and/or mouth.

The patient interface device is supported or attached to the head of the user by means of a support assembly. The support assembly may include a generally rigid frame assembly and a strap assembly. The straps may be elastic or non-elastic. The straps may have an adjustable length. As is known, a support assembly comprised exclusively of straps may bias, i.e., pull, the patient contacting cushion or other portions of the patient interface device too tightly against the user's face. Thus, a frame assembly may be used to properly position the patient contacting cushion relative to the user's face. The frame assembly is coupled to the strap assembly.

A "T-frame" assembly includes a central torus and two rearwardly extending members. That is, the rearwardly extending members are coupled to opposite lateral sides of the torus and extend toward the user's ears. A portion of the patient contacting cushion is structured to extend through the torus, thereby coupling the cushion assembly to the frame assembly. The distal tips of the frame assembly include strap couplings that are structured to be coupled to one or more straps. In this configuration, the frame assembly is concave about the user's face.

Such T-frame assemblies are not structured to be reversible. That is, the materials used to create the T-frame assembly, often a molded material, is not structured to be inverted or reversed. Further, the mask and strap couplings are disposed on one side, often the side away from the user's face, so that the coupling does not irritate the user. Accordingly, a need exists to provide a reversible support assembly for a respiratory interface device.

SUMMARY OF THE INVENTION

A reversible frame assembly for a patient interface device is provided. The reversible frame assembly includes a body, a cushion coupling, and a reversing device. The body has a first side and a second side. The body includes at least a first body member and a second body member. The body is structured to be coupled to the cushion assembly via the cushion coupling with the cushion or cushion assembly disposed on one of the first or second sides of the body. The body is structured to be disposed in one of two concave configurations, a first concave configuration, wherein the body first side is concave about at least a portion of the cushion, and a second concave configuration, wherein the body second side is concave about at least a portion of the cushion. The reversing device is structured to allow the body to move between the first configuration and second configuration.

It is a further object of this invention to provide a method of using a patient interface device including the steps of (a) coupling the cushion to the frame assembly body while the frame assembly body is in the first configuration, (b) decoupling the cushion from the frame assembly body, (c) placing the frame assembly body in the second configuration, and (d) coupling the cushion to the frame assembly body while the frame assembly body is in the second configuration.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, "a generally continuous seal" may have a gap or may gap when the user moves. As used herein, "a more complete seal" has a gap that is shorter in length than a gap of a generally continuous seal, or, is resistant to gapping when the user moves.

As used herein, "correspond" indicates that two structural components are sized to engage each other with a minimum amount of friction. Thus, an opening which corresponds to a member is sized slightly larger than the member so that the member may pass through the opening with a minimum amount of friction. This definition is modified if the two components are said to fit "snugly" together. In that situation, the difference between the size of the components is even smaller whereby the amount of friction increases.

As used herein, "rigid" means substantially unbendable. As used herein, "stiff" means structured to maintain a shape when unbiased, but bendable when exposed to a minimal bias. For example, a thin wire, such as but not limited to, a wire used in a twist tie, may be easily bent but will thereafter maintain its configuration until bent again. As used herein, a "shape maintaining member" is a member that is flexible when exposed to a bias, but returns to a selected configuration when the bias is removed; such as, but not limited to, a semi-hard plastic. As used herein, a "tension member" is a construct that has a maximum length when exposed to tension, but is otherwise substantially flexible, such as, but not limited to, a chain.

As used herein, a "coupling component" is one element of a coupling assembly. That is, a coupling assembly includes at least two elements, or components, that are structured to be coupled together. It is understood that the elements of a coupling assembly correspond to each other or are otherwise structured to be joined together. For example, in a coupling assembly, if one coupling element is a bolt, the other coupling element is a nut. Further, it is understood that the two elements of a coupling assembly may not be described at the same time.

As used herein, a "reversible flexure" is a flexure that is structured to be flexed and maintained in at least two configurations. That is, a flexible member structured to be used in a single configuration, but which can be forced into a second configuration is not a "reversible flexure."

Figure 1:
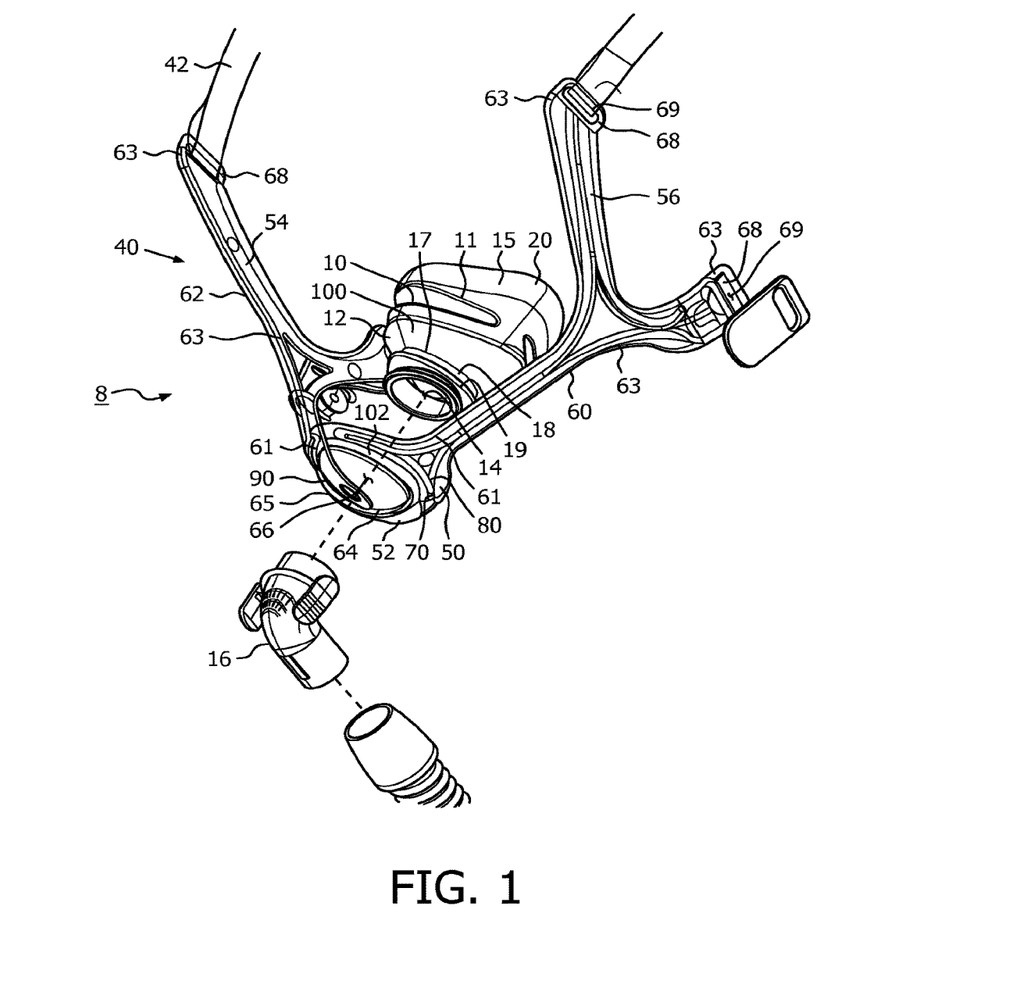
FIG. 1 is an isometric view of a respiratory interface device.

FIG. 1 shows a patient interface assembly 8 according to an exemplary embodiment of the invention. Patient interface assembly 8 includes a patient interface device 9 and a support assembly 40. Patient interface device 9 is coupled to a pressure generating system (not shown) via a patient circuit, as is conventionally known in the art. For purposes of the present invention, the pressure generating system is any device capable of generating a flow of breathing gas or providing gas at an elevated pressure. Examples of such pressure generating systems include a ventilator, CPAP device, or variable pressure device, e.g. an auto-titrating device, proportional assist ventilation (PAV®) device, proportional positive airway pressure (PPAP) device, C-Flex™ device, Bi-Flex® device, or a BiPAP® device manufactured and distributed by Philips Respironics of Murrysville, Pa., in which the pressure provided to the patient varies with the patient's respiratory cycle so that a higher pressure is delivered during inspiration than during expiration, or other pressure support device.

Patient interface device 9 includes a cushion assembly 10 that includes a body 11 with a faceplate 12 and a cushion 15, discussed below. In an exemplary embodiment, faceplate 12 is substantially rigid. In an exemplary embodiment, shown in FIG. 1, faceplate 12 is a single piece structured to cover the user's nose. That is, patient cushion assembly 10 has a peripheral contour that is structured to extend over a user's nose and mouth. In this embodiment, body 11 is coextensive with faceplate 12. It is understood that this is an exemplary embodiment and cushion assembly 10 may be structured to extend over the user's nose and mouth, or, just the user's mouth. Further, it is understood that the faceplate 12 may be made from a soft or flexible material. Faceplate 12 defines lower opening 14. Lower opening 14 can function as a gas inlet. Gas inlet (lower opening 14) can be coupled to a coupling device 16, such as a swivel conduit, for carrying gas such as air between cushion assembly 10 and an external gas source (not shown), such as a blower, or any other suitable device. It is to be further understood that cushion assembly 10 can be formed form a unitary element rather than an assembly of components.

It is contemplated that the external gas source can encompass, without limitation, any gas delivery or gas generation system capable of supplying gas for consumption by a user. Non-limiting examples of various gas delivery therapies can include but are not limited to continuous positive airway pressure (CPAP) therapy, auto-titration positive airway pressure therapy, and bi-level positive airway pressure (BiPAP) therapy, as noted above. The particular coupling device 16, shown in FIG. 1, is not meant to be limiting and it should be understood that the present invention contemplates a variety of different coupling devices that could be attached, either permanently or selectively, to lower opening 14 to carry gas to or from cushion assembly 10. Thus, a variety of coupling devices (e.g., with or without swivels on one or both ends, and with or without an exhalation system formed integral to the device) may be substituted for coupling device 16.

Cushion assembly 10 further includes a support assembly coupling 18. Support assembly coupling 18 is structured to be coupled to a support assembly 40. For support assembly 40, and more specifically frame assembly 50, discussed below, support assembly coupling 18 is a coupling structured to interface with a closed, flexible loop or torus shaped member 65, as discussed below. Accordingly, support assembly coupling 18 may be a loop-like groove in faceplate 12. The outer edge of the groove has a greater cross-sectional area than torus shaped member 65 and frame assembly 50 must be stretched over faceplate 12 so that torus shaped member 65 may be disposed in the groove. Further, the contour of the outer surface of faceplate 12 may form a platform 17. Platform 17 is structured to abut, and thereby effect, the shape a frame assembly 50, discussed below. Further, cushion assembly 10 may include a retaining flange 19 extending partially over platform 17. In an exemplary embodiment, retaining flange 19 extends generally parallel to platform 17, thus forming the groove. Accordingly, if platform 17 is concave relative to the user's face, then retaining flange 19 is also concave relative to the user's face. Platform 17 and retaining flange 19 may be first reversing device components 110, as discussed below.

Cushion 15 is structured to extend from faceplate 12 toward the user's face and generally defines the depth of cushion assembly 10. Cushion 15 includes a cushion body 20 made from a flexible material. Cushion 15 is structured to engage the user's face and provide a generally continuous seal. This seal may be improved to be a more complete seal if cushion assembly 10 is maintained in an orientation that is generally tangent relative to the user's face. The bias that causes cushion 15 to engage the user's face is created by support assembly 40.

Support assembly 40 includes at least one strap 42 and a frame assembly 50. Straps 42 are tension members. As shown, support assembly 40 includes two straps 42—the claims, however, are not limited to this configuration. Each strap 42 is structured to extend about the user's head. As is known, support assembly straps 42 may form a web (not shown) having straps 42 in any number of configurations. Straps 42 may be made from an elastic or non-elastic material.

Frame assembly 50 is a reversible frame assembly 50. Reversible frame assembly 50 includes a body 52 having a first side 54 and a second side 56. Frame assembly body 52 includes at least a first substantially flat, elongated member 60 and a second substantially flat, elongated member 62, a cushion assembly coupling 64, and a reversing device 70. Frame assembly body 52 is structured to be coupled to cushion assembly 10 at the cushion assembly coupling 64 with cushion assembly 10 substantially disposed on one of body first or second sides 54, 56. That is, in an exemplary embodiment, cushion assembly coupling 64 is a torus shaped member 65 defining an opening 66. As used herein "torus" is construed broadly as a closed loop which may not be symmetric. The torus shaped member 65 may be a unitary body, a partially unitary body, or a non-unitary body having elements that are coupled together. Opening 66 is sized to allow a portion of cushion assembly 10 to extend therethrough, as described below. Other than the portion of cushion assembly 10 extending through opening 66, cushion assembly 10 is disposed on one of body first or second sides 54, 56.

As discussed below, frame assembly body 52, as well as first body member 60 and second body member 60 are "stiff" or are "shape maintaining members." Thus, first body member 60 and second body member 62 are substantially flat when unbiased. It is understood that in use, and under bias from straps 42, first body member 60 and second body member 62 may not be generally flat. Each of first body member 60 and second body member 62 are coupled at a proximal end 61 to opposing lateral sides of torus shaped member 65 and extend outwardly therefrom. First body member 60 and second body member 62 each have a distal end 63 that includes a strap coupling 68. As shown, first body member 60 and second body member 62 are generally "T-shaped;" that is, the distal ends 63 of each body member 60, 62 are split into a plurality of distal ends 63. In this configuration, each distal end 63 of first body member 60 and second body member 62 include a strap coupling 68. Strap couplings 68 are reversible, as described below, and, in one exemplary embodiment, are slots 69 through which straps 42 may be looped. Thus, straps 42 may be coupled to frame assembly 50 and the support assembly 40 is structured to encircle a user's head.

Frame assembly 50, and more specifically frame assembly body 52, is structured to be disposed in one of two generally concave configurations, a first concave configuration, wherein body first side 54 is concave about cushion assembly 10, and a second concave configuration, wherein body second side 56 is concave about cushion assembly 10. As discussed below, frame assembly body 52 is made from flexible and semi-flexible materials. Thus, as used herein, "generally concave" means a configuration that is, in a general manner, concave. Thus, first body member 60 and second body member 62, while generally flat and not curved, are part of the "generally concave" configuration of frame assembly body 52 as the whole of frame assembly body 52 is "generally concave." That is, with cushion assembly 10 disposed in torus shaped member 65, first body member 60 and second body member 60 extend generally laterally outward from torus shaped member 65. With frame assembly body 52 in a generally concave configuration, however, first body member 60 and second body member 62 each extend rearwardly. In use, first body member 60 and second body member 62 each extend toward one of the user's ears. Thus, frame assembly 50, and more specifically first body member 60 and second body member 62, partially encircle a user's head.

Figure 2:
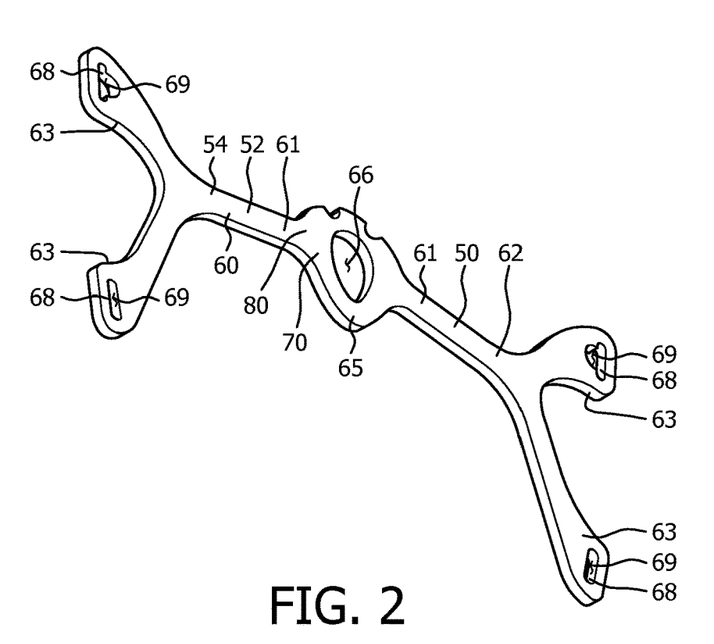
FIG. 2 is an isometric view of one embodiment of a frame assembly.

Reversing device 70 is structured to allow frame assembly body 52 to move between the first configuration and second configuration. Reversing device 70 may further be structured to maintain frame assembly body 52 in one of the first configuration and second configuration. For example, in one exemplary embodiment, shown in FIG. 2, frame assembly body 52 is substantially flat. That is, torus shaped member 65, as well as, first member 60 and second member 62 are flat and, if placed on a flat surface, may be disposed in generally the same plane. In this embodiment, reversing device 70 includes a reversible flexure 80 disposed about at cushion assembly coupling 64. As used herein, "about at" means that reversible flexure 80 may be part of cushion assembly coupling 64 or disposed adjacent thereto, i.e. at the coupling between cushion assembly coupling 64 and each of first body member 60 and second body member 62. Thus, reversible flexure 80 is incorporated into cushion assembly coupling 64 in that cushion assembly coupling 64 is stiff or shape maintaining, but may be curved about cushion assembly 10 in either direction. That is, cushion assembly coupling 64 may be placed in a generally concave configuration about cushion assembly 10 with either frame assembly body first side 54 or second side 56 being the concave surface.

As noted above, cushion assembly 10 includes support assembly coupling 18 on faceplate 12, as shown in FIG. 1. When frame assembly 50, and more specifically cushion assembly coupling 64, is coupled to cushion assembly 10, and more specifically to support assembly coupling 18, the flexible nature of frame assembly body 52, as discussed below, allows frame assembly body 52 to bend about faceplate 12; this is especially true when the bias of straps 42 is applied. Thus, frame assembly body 52 may be coupled to support assembly coupling 18 with body first side 54 abutting faceplate 12 and frame assembly body 52 will follow the contour of faceplate 12 thereby becoming concave about at least a portion of cushion assembly 10. That is, in this first configuration, body first side 54 is concave about a least a portion of cushion assembly 10. Conversely, frame assembly body 52 may be coupled to support assembly coupling 18 with body second side 56 abutting faceplate 12 and frame assembly body 52 will follow the contour of faceplate 12 thereby becoming concave about at least a portion of cushion assembly 10. In this second configuration, body second side 56 is concave about at least a portion of cushion assembly 10. A user may switch between configurations by positioning cushion assembly 10 on a selected side before coupling cushion assembly 10 to frame assembly 50. Thus, frame assembly 50 is reversible.

In another exemplary embodiment, reversing device 70 is structured to maintain frame assembly body 52 in one of the first configuration and second configuration. As shown in FIG. 1, torus shaped member 65 is shaped as a hollow frustum 90. As used herein, "frustum" is any truncated, generally conic section or similar shape, e.g. a truncated pyramid. As discussed below, frustum 90 is flexible. As is known, flexible frustum 90 may be inverted. Moreover, because frustum 90 maintains its conic properties even when inverted, frustum 90 tends to stay in the inverted configuration. Thus, when frustum 90 is in a first configuration, with first body member 60 and second body member 62 coupled to lateral edges of frustum 90, with each extending rearwardly, frame assembly 50 is generally concave. Frustum 90 may be inverted and will maintain the inverted conical shape. As first body member 60 and second body member 62 are coupled to the lateral edges of frustum 90, in the second configuration, frame assembly 50 is also generally concave. Moreover, as some force is required to invert frustum 90, frustum 90 maintains frame assembly 50 in either the first or second configuration. That is, once frustum 90 is in either the first or second configuration, meaning frame assembly 50 is in the same configuration, then frustum 90 tends to stay in that configuration. Thus, the user selects the configuration of the frame assembly 50 and couples cushion assembly 10 to whichever side is the concave side. That is, either body first side 54 or body second side 56 may be the concave side. As such, frame assembly 50 is reversible.

In the first embodiment above, wherein torus shaped member 65 is generally flat, reversing device 70 is just the reversible flexure 80. In that embodiment, frame assembly body 52, when biased, will follow the contour of faceplate 12 thereby becoming concave about at least a portion of cushion assembly 10. Maintaining the concave shape, however, relies upon the bias of straps 42. In another embodiment similar thereto, reversing device 70 is structured to maintain frame assembly body 52 in one of the first configuration and second configuration. This is accomplished by providing a first reversing device component 100 on cushion assembly 10 and a second reversing device component 102 on frame assembly 50. Second reversing device component 102 is a reversible flexure 80 as described above. First reversing device component 100 includes concave platform 17 and retaining flange 19.

As noted above, retaining flange 19 extends partially over platform 17. Thus, platform 17 and retaining flange 19 define a groove. When frame assembly body 52 is disposed between platform 17 and retaining flange 19, platform 17 and retaining flange 19 shape frame assembly body 52. Thus, if platform 17 and retaining flange 19 extend in a concave profile, then frame assembly body 52 is maintained in a concave shape. That is, torus shaped member 65 defines an opening 66 in the frame assembly body 52 that is cushion assembly coupling 64. Frame assembly body 52 at cushion assembly coupling 64 is structured to fit snuggly between first reversing component device retaining flange 19 and the first reversing device component platform 17. In this configuration, first reversing device component 100 engages both frame assembly body first and second sides 54, 56 and causes frame assembly body first and second sides 54, 56 to extend over a curve similar to the curve defined by platform 17 and retaining flange 19. Thus, frame assembly body 52 is maintained in a selected configuration. That is, frame assembly body 52 may be positioned with either the first or the second side 54, 56 abutting platform 17, so frame assembly body 52 may be in either the first or second configuration as described above.

Figure 3:
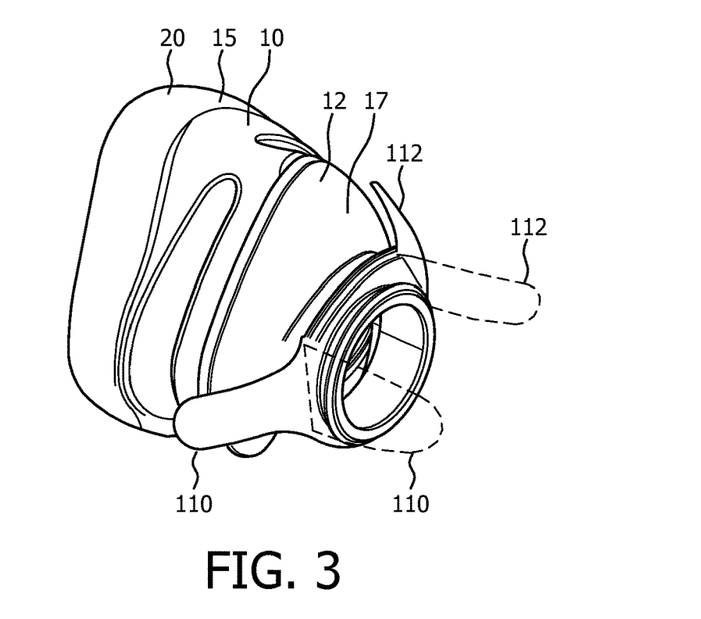
FIG. 3 is an isometric view of another embodiment of a reversing device.

In another exemplary embodiment, first reversing device component 100 may be enhanced so as to better position frame assembly body 52. That is, as shown in FIG. 3, first reversing component device retaining flange 19 includes an elongated lateral first portion 110 and an elongated lateral second portion 112. Each of first reversing component device retaining flange first and second portions 110, 112 are pivotally coupled to cushion assembly 10 and are structured to move between a first narrow configuration (shown in ghost), wherein first reversing component device retaining flange 19 is sized to pass through reversible frame assembly coupling opening 66, and a second wide configuration, wherein first reversing component device retaining flange 19 is sized to have a cross-sectional area that is larger than reversible frame assembly coupling opening 66. That is, first reversing component device retaining flange first and second portions 110, 112 are similar to wings coupled to cushion assembly 10. When the first reversing component device retaining flange first and second portions 110, 112 are lifted to the point where they almost touch, first reversing component device retaining flange 19 is sized to pass through reversible frame assembly coupling opening 66. When the first reversing component device retaining flange first and second portions 110, 112 are brought down, first reversing component device retaining flange 19 is sized to have a cross-sectional area that is larger than reversible frame assembly coupling opening 66. Moreover, in the second configuration, first reversing component device retaining flange first and second portions 110, 112 have a larger area that is contact with frame assembly body 52 than in the embodiment wherein the first reversing component device retaining flange 19 does not have elongated lateral first and second portions 110, 112. Further, first reversing component device retaining flange first and second portions 110, 112 may be biased toward their second configuration. Thus, first reversing component device retaining flange first and second portions 110, 112 will maintain frame assembly 50 in a concave configuration.

Figure 4A:
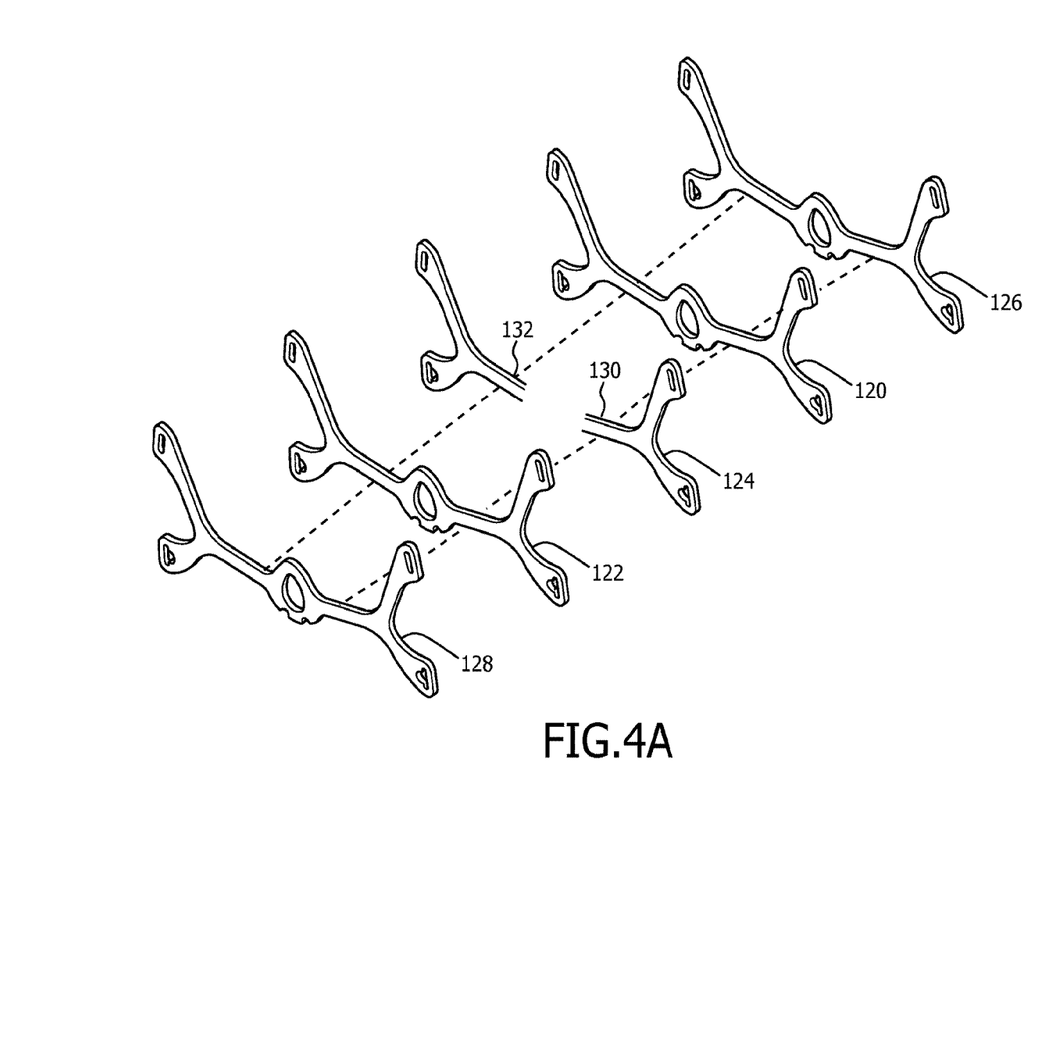
FIG. 4A is an exploded view of a frame assembly.

As noted above, frame assembly body 52 is flexible. In an exemplary embodiment, frame assembly body 52 is "stiff" or a "shape maintaining member." It is noted that frustum 90 made of a "stiff" or a "shape maintaining member" will maintain itself in a selected configuration. That is, frustum 90 made of a "stiff" or a "shape maintaining member" that is inverted will maintain itself in the inverted configuration and not return to the original configuration. Thus, the shape is maintained as frustum 90, but the orientation may change. As shown in FIG. 4A, frame assembly body 52 includes at least a first material member 120, a second material member 122, and a support member 124. As shown, there are additional material members, a third material member 126 and a forth material member 128.

In an exemplary embodiment, first material member 120 and second material member 122 are silicone, and, third material member 126 and forth material member 128 are fabric. Support member 124 may be bifurcated as shown in FIG. 4. It is noted that first material member 120 and second material member 124 are, in an exemplary embodiment, unitary bodies. First material member 120 and second material member 122 are flexible and therefore may be stretched over support assembly coupling 18. First material member 120 and second material member 122 may have different characteristics or identical characteristics, i.e. first material member 120 and second material member 122 may be made from the same material, similar materials, or different materials. For example, first material member 120 may be fabric covered silicon and second material member 122 may be exposed silicone. Further, material members 120, 122, 12, 126, 128 may be coupled by any of an adhesive, flame-lamination, multi-shot molding, over-molding, sewing, mechanical interlock, or use of a self-bonding material.

Further, the characteristics of first material member 120 and second material member 122 include their appearance and texture. For example, first material member 120 may be one color or pattern and second material member 122 may be another color or pattern. The colors and/or patterns may be incorporated into a material, such as, but not limited to, grooves molded into a silicone body or stitching on a fabric body, or the patterns may be printed on a material, such as, but not limited to, a fabric body. Thus, patterns can have visual and/or tactual characteristics, in that the pattern can not only be visually apparent, but may be felt as well. As an exemplary embodiment (not shown), a material member may substantially be a silicon body of one color with raised rubber nubs of another color. Further, the rubber nubs may be disposed in a pattern. Such a configuration may act as a non-slip surface. Thus, first material member 120 may have an outer surface that is a non-slip texture while second material member 122 may be a substantially smooth fabric. In this configuration, the user may choose to have either first material member 120 or second material member 122, with their associated characteristics exposed for others to see while the other material member 120, 122 will engage the user's face. First material member 120 and second material member 122 may be selected from the group including silicones, rubbers, gels, thermoplastics, foams and textiles. Thus, as used herein, a material member's 120, 122 "characteristics" include, the type of material and the appearance of the material, including color, patterns, designs, or other indicia, and texture.

First and third material members 120, 126 are disposed on frame assembly body first side 54 and second and fourth material members 122, 128 are disposed on frame assembly body second side 56. Support member 124 is disposed between first material member 120 and second material member 122. Further, first, second, third and fourth material members 120, 122, 126, 128 are shaped to substantially conform to the shape of support member 124. First material member 120 and second material member 122 may be applied to support member 124, adhered to support member 124, or formed as a unitary body with support member 124. First material member 120 and second material member 122 may, however, extend beyond the edges of support member 124 thereby providing flexibility to frame assembly body 52.

Figure 4B:
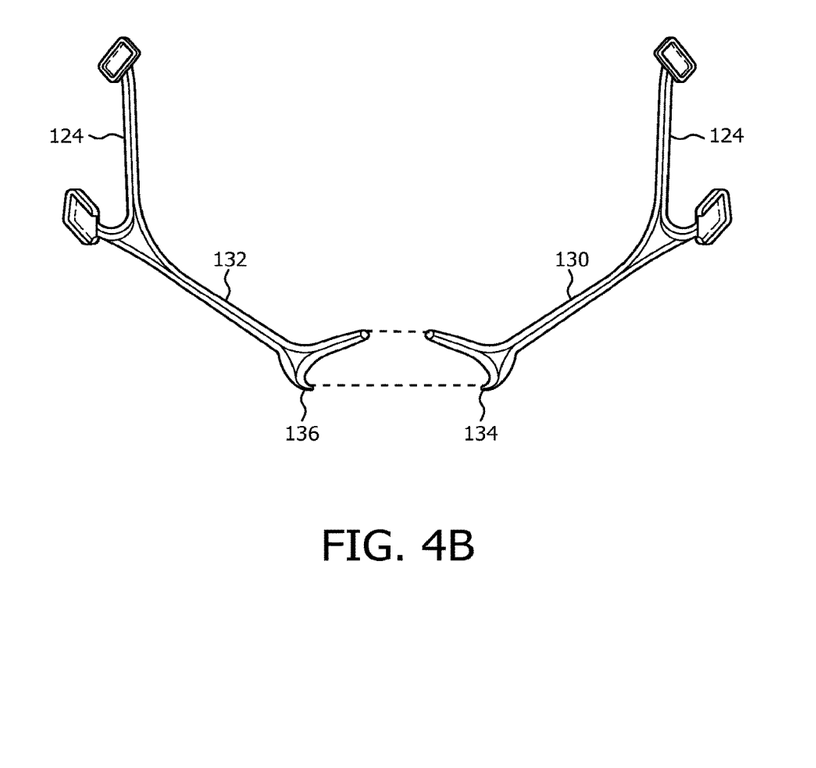
FIG. 4B is an isometric view of an alternate support member.

That is, support member 124 is more firm than first, second, third and fourth material members 120, 122, 126, 128, but still flexible. Support member 124 gives frame assembly body 52 its stiffness or the ability to return to a specific shape. Support member 124 includes a first side member 130 and a second side member 132. Support member first side member 130 defines first body member 60, and may define a first portion 134 of torus shaped member 65 (as shown in FIG. 4B). Support member second side member 132 defines second body member 62, and may define a second portion 136 of torus shaped member 65 (as shown in FIG. 4B). Thus, when torus shaped member 65 is a frustum 90, support member first side member 130 defines a first portion 134 of frustum 90 and support member second side member 132 defines a second portion 136 of frustum 90. Thus, support member first and second side members 130, 132 each have a shape, such as the "T shape" of first and second body members 60, 62, discussed above, as well as circular portions 134, 136.

When assembled, first side member 130 and second side member 132, or support member circular portions 134, 136, may not be directly coupled. That is, first material member 120 and second material member 122 may extend over a gap between first side member 130 and second side member 132, or support member circular portions 134, 136. In this configuration, torus shaped member 65 is very flexible as first side member 130 and second side member 132, or support member circular portions 134, 136, are not directly coupled. Thus, the flexible nature of first material member 120 and second material member 122 provide for the reversible flexure 80 disposed about cushion assembly coupling 64. Further, when support member 124 is bifurcated and support member circular portions 134, 136 are not unitary, that is support member circular portions 134, 136 are coupled, the ease of inverting frustum 90 is increased.

In an exemplary embodiment, shown in FIG. 4A, all material members and support member 120, 122, 124, 126, 128 are substantially planar. Thus, frame assembly body 52 is substantially planar. Moreover, the frame assembly body first side 54 and frame assembly body second side 56 each have a profile, or cross-sectional shape. Frame assembly body first side 54 profile and frame assembly body second side 56 profile are substantially similar. It is noted that when a frame assembly 50 is not reversible, the profiles of first and second side 54, 56 are different. For example, a non-reversible frame assembly may include snaps or a hook-and-loop fastener as a cushion assembly coupling device 16. These fasteners are located on a single side of the frame assembly 50, i.e. the profile on first and second sides 54, 56 is different, as there is no need to reverse the frame assembly 50. The present frame assembly 50 utilizes couplings such as openings, e.g. the torus shaped member opening 66 as a coupling device 16, as such couplings have a profile that is reversible.

Figure 5:
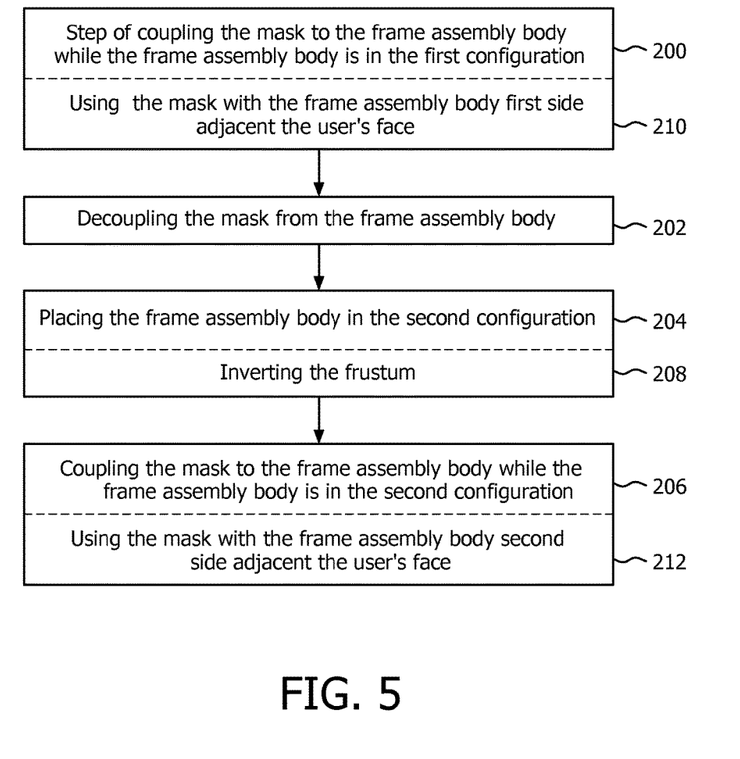
FIG. 5 is a flow chart of the method steps.

Accordingly, as shown in FIG. 5, a method of using patient interface device 8 having a reversible frame assembly 50, as described above, includes the steps of coupling 200 the cushion assembly to the frame assembly body while the frame assembly body is in the first configuration, decoupling 202 the cushion assembly from the frame assembly body, placing 204 the frame assembly body in the second configuration, and coupling 206 the cushion assembly to the frame assembly body while the frame assembly body is in the second configuration. If the reversing device 70 includes a flexible, hollow frustum 90, the step of placing 204 the frame assembly body in the second configuration includes the step of inverting 208 the frustum 90. Further the steps of coupling 200 the cushion assembly to the frame assembly body while the frame assembly body is in the first configuration and coupling 206 the cushion assembly to the frame assembly body while the frame assembly body is in the second configuration may include, respectively, the further steps of using 210 the cushion assembly with the frame assembly body first side adjacent the user's face, and, using 212 the cushion assembly with the frame assembly body second side adjacent the user's face.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of using a patient interface assembly including a patient interface device and a support assembly, the patient interface device includes a cushion assembly having a support assembly coupling, the support assembly including at least one strap and a reversible frame assembly, the reversible frame assembly including a frame assembly body having a first side and a second side, the frame assembly body including at least a first substantially flat, elongated member and a second substantially flat elongated member, a cushion assembly coupling, and a reversing device, each of the first body member and the second body member coupled at a proximal end to the cushion assembly coupling, the frame assembly body structured to be coupled to the cushion assembly at the cushion assembly coupling with the cushion assembly substantially disposed on one of the first or second sides of the frame assembly body, the frame assembly body structured to be disposed in one of two concave configurations, a first concave configuration, wherein the body first side is concave about at least a portion of the cushion assembly, and a second concave configuration, wherein the body second side is concave about at least a portion of the cushion assembly, and the reversing device structured to allow the frame assembly body to move between the first configuration and second configuration, the method comprising the steps of:

coupling the cushion assembly to the frame assembly body while the frame assembly body is in the first configuration;

decoupling the cushion assembly from the frame assembly body;

placing the frame assembly body in the second configuration; and coupling the cushion assembly to the frame assembly body while the frame assembly body is in the second configuration.

2. The method of claim 1, wherein the reversing device includes a flexible, hollow frustum and wherein the step of placing the frame assembly body in the second configuration includes the step of inverting the frustum.

3. The method of claim 1, wherein the steps of coupling the cushion assembly to the frame assembly body while the frame assembly body is in the first configuration and coupling the cushion assembly to the frame assembly body while the frame assembly body is in the second configuration includes the steps of:

using the cushion assembly with the frame assembly body first side adjacent the user's face; and using the cushion assembly with the frame assembly body second side adjacent the user's face.

* * * * *